US012599669B2

(12) United States Patent
Sloey

(10) Patent No.: US 12,599,669 B2
(45) Date of Patent: Apr. 14, 2026

(54) USE OF LOW MOLECULAR WEIGHT POLYVINYLPYRROLIDONE (PVP) TO REDUCE VISCOSITY OF HIGH CONCENTRATION PROTEIN FORMULATIONS

(71) Applicant: AMGEN INC., Thousand Oaks, CA (US)

(72) Inventor: Christopher James Sloey, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 15 days.

(21) Appl. No.: 17/605,512

(22) PCT Filed: Apr. 22, 2020

(86) PCT No.: PCT/US2020/029328

§ 371 (c)(1),
(2) Date: Oct. 21, 2021

(87) PCT Pub. No.: WO2020/219550

PCT Pub. Date: Oct. 29, 2020

(65) Prior Publication Data

US 2022/0226477 A1 Jul. 21, 2022

Related U.S. Application Data

(60) Provisional application No. 62/837,647, filed on Apr. 23, 2019.

(51) Int. Cl.

| | |
|---|---|
| ***A61K 47/32*** | (2006.01) |
| ***A61K 9/00*** | (2006.01) |
| ***A61K 9/19*** | (2006.01) |
| ***A61K 38/00*** | (2006.01) |

(52) U.S. Cl.

CPC ............ *A61K 47/32* (2013.01); *A61K 9/0019* (2013.01); *A61K 9/19* (2013.01); *A61K 38/00* (2013.01)

(58) Field of Classification Search

CPC ........ A61K 47/32; A61K 9/0019; A61K 9/19; A61K 38/00; A61K 47/183

See application file for complete search history.

(56) References Cited

U.S. PATENT DOCUMENTS

| | | | | |
|---|---|---|---|---|
| 2014/0044727 A1* | 2/2014 | Monck | A61K 47/12 | 424/145.1 |
| 2017/0209587 A1 | 7/2017 | Tarrand et al. | | |
| 2018/0237501 A1* | 8/2018 | Sloey | C07K 1/36 | |

FOREIGN PATENT DOCUMENTS

| | | |
|---|---|---|
| JP | 2002516612 A | 12/1998 |
| JP | 2005516971 A | 7/2003 |
| JP | 2010248271 A | 9/2003 |
| JP | 2010524948 A | 10/2008 |
| JP | 2012512162 A | 8/2010 |
| WO | 2016/065181 A1 | 4/2016 |
| WO | 2018/201064 A1 | 11/2018 |

OTHER PUBLICATIONS

Maggio et al. (The shear rate and concentration dependence of viscosity in concentrated solutions of PVP and Bovine Mucin, Contact Lens & Anterior Eye, 2018), (Year: 2018).*

Buhler (Polyvinylpyrrolidone Excipients for Pharmaceuticals, Springer 2005). (Year: 2005).*

Allmendinger (Rheological investigation of manufacturability and injectability of highly concentrated monoclonal antibody formulation , Dissertation, 2014) (Year: 2014).*

Fisher Scientific (Polyvinylpyrrolidone Product, SDS created Oct. 25, 2014). (Year: 2014).*

Ausubel FM. 1987. Current protocols in molecular biology. Brooklyn, N.Y. Media, Pa.: Greene Pub. Associates; J. Wiley, order fulfillment. 2 volumes (loose-leaf).

BASF, "Kollidon®—The Original" Oct. 2014, Brochure in 9 pp.

Bühler V.: "Kollidon?—Polyvinylpyrrolidone for the pharmaceutical industry, 4th edition" In: "Kollidon?—Polyvinylpyrrolidone for the pharmaceutical industry, 4th edition", Mar. 1998 (Mar. 1998), BASF Aktiengesel 1 schaft, XP055275311, pp. 2 pp. 5, 6, 15-48, 70, 71, 109-116.

Bühler V.: Polyvinylpyrrolidone Excipients for the Pharmaceuticals, 2005, Springer, New York, 258 pp.

Gombotz et al., "The stabilization of a human I gM monoclonal antibody with poly(vinylpyrrolidone)", Pharmaceutical Research, Springer New York LLC, US, vol. 11, No. 5, 1994, pp. 624-632.

Haaf et al., Polymers of N-Vinylpyrrolidone: Synthesis, Characterization and Use. Polymer Journal 17: 143-152 (1991).

International Preliminary Report on Patentability & Written Opinion issued Sep. 28, 2021 for PCT/US2020/029328.

International Search Report and the Written Opinion of the International Searching Authority mailed Jul. 21, 2020 for PCT/US2020/029328.

Kamerzell TJ, Esfandiary R, Joshi SB, Middaugh CR, Volkin DB. 2011. Protein-excipient interactions: mechanisms and biophysical characterization applied to protein formulation development. *Adv Drug Deliv Rev* 63: 1118-59.

Kostelny SA, Cole MS, Tso JY. 1992. Formation of a bispecific antibody by the use of leucine zippers. *J Immunol* 148: 1547-53.

Krishnan, Sampathkumar et al.: "Development of Formulations for Therapeutic Monoclonal Antibodies and Fc Fusion Proteins" In: "Formulation and process development strategies for manufacturing biopharmaceuticals," Jul. 26, 2010 (Jul. 26, 2010), Wiley, New York.

(Continued)

*Primary Examiner* — Robert A Wax
*Assistant Examiner* — John Seungjai Kwon
(74) *Attorney, Agent, or Firm* — Scott Siera

(57) ABSTRACT

Disclosed herein are pharmaceutical compositions (formulations) having reduced viscosity, using a low molecular weight polyvinylpyrrolidone (povidone) in the case of high therapeutic protein concentration (≥70 mg/ml) formulations. The addition of arginine, such as arginine monohydrochloride or N-acetyl arginine, can further reduce viscosity. Appropriate therapeutic proteins include antibodies, such as monoclonal antibodies, and derivatives, fragments, and analogues thereof.

15 Claims, 4 Drawing Sheets

(56) References Cited

OTHER PUBLICATIONS

Powell MF, Nguyen T, Baloian L. 1998. Compendium of excipients for parenteral formulations. *PDA J Pharm Sci Technol* 52: 238-311.
Sambrook J, Russell DW. 2001. *Molecular cloning : a laboratory manual.* 3rd Edition. Cold Spring Harbor, N.Y.: Cold Spring Harbor Laboratory Press.
Songsivilai S, Lachmann PJ. 1990. Bispecific antibody: a tool for diagnosis and treatment of disease. *Clin Exp Immunol* 79: 315-21.
Ward ES, Gussow D, Griffiths AD, Jones PT, Winter G. 1989. Binding activities of a repertoire of single immunoglobulin variable domains secreted from *Escherichia coli. Nature* 341: 544-6.
Wu X, Demarest SJ. 2018. Building blocks for bispecific and trispecific antibodies. *Methods.*
Wu X, Yuan R, Bacica M, Demarest SJ. 2018. Generation of orthogonal Fab-based trispecific antibody formats. *Protein Eng Des Sel* 31: 249-56.

* cited by examiner

USE OF LOW MOLECULAR WEIGHT POLYVINYLPYRROLIDONE (PVP) TO REDUCE VISCOSITY OF HIGH CONCENTRATION PROTEIN FORMULATIONS

CROSS-REFERENCE TO RELATED APPLICATIONS

This application is a national stage application under 35 U.S.C. § 371 of International Application No. PCT/US2020/029328, having an international filing date of Apr. 22, 2020, which claims the benefit of, and priority to U.S. Provisional Application No. 62/837,647, filed on Apr. 23, 2019, which is incorporated in its entirety by reference herein.

FIELD OF THE INVENTION

The presented subject matter relates to the field(s) of pharmaceutical formulations. Specifically, the presented subject matter relates to high concentration therapeutic protein formulations, and compositions and methods of reducing viscosity thereof using polyvinylpyrrolidone (PVP).

BACKGROUND

Pharmaceutically active proteins, such as antibodies, are frequently formulated in liquid solutions, particularly for parenteral injection. For products that need to be administered via a subcutaneous route, for example, for use in self administration, formulations in delivery volumes greater than 1-2 milliliters are often not well tolerated. In such cases, highly concentrated protein formulations can meet the desirable smaller dose volume. The high dose and small volume requirements of such administration means that the protein therapeutic can reach concentrations of upwards of 100 mg/mL or much more.

Highly concentrated protein formulations can pose many challenges to the manufacturability and administration of protein therapeutics. One challenge posed by some highly concentrated protein formulations is increased viscosity. High viscosity formulations are difficult to handle during manufacturing, including at the bulk and filling stages. High viscosity formulations are also difficult to draw into a syringe and inject, making administration to the patient difficult and unpleasant. There is a need in the pharmaceutical industry to identify compounds that are useful for reducing viscosity of highly concentrated protein formulations, to develop methods of reducing the viscosity of such formulations, and to provide pharmaceutical formulations with reduced viscosity.

SUMMARY

In a first aspect, disclosed herein are compositions comprising a concentration of a therapeutic protein and polyvinylpyrrolidone (PVP), wherein the viscosity of the composition comprising the PVP is less than a composition comprising the same concentration of the therapeutic protein, but the PVP is absent.

In a second aspect, disclosed herein are compositions comprising a concentration of a therapeutic protein and PVP, wherein the viscosity of the composition is less than or equal to 80 cP. The viscosity can be, for example, in cP, 70, 40, or 20.

In both the first and second aspects, the viscosity of the composition can be read at 25° C. and reported at a shear rate of 1000/s, using for example, an AR-G2 cone and plate rheometer from TA Instruments of New Castle, Del. (USA). The concentration of the therapeutic protein is greater than 70 mg/mL, such as from about 140 mg/mL to about 250 mg/mL, including, for example, about 145, 160, 198, 200, 238, and 249 mg/mL. The PVP can be present at a concentration from about 0.3% to about 10%, such as from about 1%, 2%, 3%, 4%, 5%, 6%, 7%, 8%, 9%, and 10%, and increments between. The stability of the therapeutic protein is about the same when compared to a control lacking PVP; stability can be assessed by the presence of at least one selected from the group consisting of high molecular weight species, low molecular weight species, dimers, and oligomers of the therapeutic protein. In some sub-aspects, the therapeutic protein comprises at least one complementarity determining region (CDR), and can be, for example, an antibody, such as a monoclonal antibody (mAb). Furthermore, the therapeutic protein comprising at least one CDR can be an antigen-binding fragment or derivative of an antibody. The antigen binding fragment can be one selected from the group consisting of an Fab' fragment, an F'(ab)2 fragment, and an Fv fragment. In the case of a derivative of the antibody, the derivative can be selected from the group consisting of a humanized antibody, a chimeric antibody, a multi-specific antibody, a maxibody, a BiTE® molecule, a single chain antibody, a diabody, and a peptibody. The PVP has a K value of 12-17, such as 12 or 17. The PVP can have a weight average molecular weight of 11,000 Da or less, such as from about 2,000 Da to about 25,000 Da or such as from about 2,000 Da to about 3,000 Da. The composition can be formulated for delivery to a patient. The formulation can have a pH between about 4.0 to about 8.0, such as about 4.6 to about 5.4. Furthermore, the composition can comprise arginine, such as N-acetyl arginine (at a concentration of, for example, 10 mM), or a salt of arginine, such as arginine monohydrochloride (Arg HCl), arginine glutamate, or arginine acetate. In the case of Arg HCl, the Arg HCl can be present at about 67 mM. In one sub-aspect, wherein the composition comprises Arg HCL, the PVP can be present at about 1%.

In a sub-aspect of this first and second aspects, disclosed herein are methods of preparing a lyophilized powder comprising the step of lyophilizing the composition of the first or second aspects.

In a third aspect, disclosed herein are methods of reducing the viscosity of a pharmaceutical formulation comprising a therapeutic protein, comprising the step of combining the therapeutic protein with a viscosity-reducing concentration of PVP. The viscosity of the composition made by the methods of this third aspect is less than or equal to 80 cP. The viscosity can be, for example, in cP, 70, 40, or 20.

In this third aspect, the compositions made by the methods of this aspect, the viscosity can be read at 25° C. and reported at a shear rate of 1000/s, using for example, an AR-G2 cone and plate rheometer from TA Instruments of New Castle, Delaware (USA). The concentration of the therapeutic protein is greater than 70 mg/mL, such as from about 140 mg/mL to about 250 mg/mL, including, for example, about 145, 160, 198, 200, 238, and 249 mg/mL. The PVP can be present at a concentration from about 0.3% to about 10%, such as from about 1%, 2%, 3%, 4%, 5%, 6%, 7%, 8%, 9%, and 10%, and increments between. The stability of the therapeutic protein is about the same when compared to a control lacking PVP; stability can be assessed by the presence of at least one selected from the group consisting of high molecular weight species, low molecular weight species, dimers, and oligomers of the therapeutic protein. In some sub-aspects, the therapeutic protein comprises at least one complementarity determining region (CDR), and can be, for example, an antibody, such as a monoclonal antibody (mAb). Furthermore, the therapeutic protein comprising at least one CDR can be an antigen-binding fragment or derivative of an antibody. The antigen binding fragment can be one selected from the group consisting of an Fab' fragment, an F'(ab)2 fragment, and an Fv fragment. In the case of a derivative of the antibody, the derivative can be selected from the group consisting of a humanized antibody, a chimeric antibody, a multi-specific antibody, a maxibody, a BiTE® molecule, a single chain antibody, a diabody, and a peptibody. The PVP has a K value of 12-17, such as 12 or 17. The PVP can have a weight average molecular weight of 11,000 Da or less, such as from about 2,000 Da to about 25,000 Da or such as from about 2,000 Da to about 3,000 Da. The composition can be formulated for delivery to a patient. The formulation can have a pH between about 4.0 to about 8.0, such as about 4.6 to about 5.4. Furthermore, the composition can comprise arginine, such as N-acetyl arginine (at a concentration of, for example, 10 mM), or a salt of arginine, such as arginine monohydrochloride (Arg HCl), arginine glutamate, or arginine acetate. In the case of Arg HCl, the Arg HCl can be present at about 67 mM. In one sub-aspect, wherein the composition comprises Arg HCL, the PVP can be present at about 1%.

In a fourth aspect, disclosed herein are lyophilized powders comprising a therapeutic protein and PVP, wherein the PVP is present at a weight:weight concentration effective to reduce viscosity after reconstitution with a diluent. In related sub-aspects, the PVP is present at a concentration of between about 100 μg/mg therapeutic protein to about 1 mg/mg therapeutic protein. For example, the PVP is present at a concentration between about 200 μg/mg to about 500 μg/mg therapeutic protein to about 1 mg/mg therapeutic protein before reconstitution with a diluent.

The viscosity of the compositions when the lyophilized powder is reconstituted with a diluent of this fourth aspect is less than or equal to 80 cP. The viscosity can be, for example, in cP, 70, 40, or 20.

In this fourth aspect, for the compositions when the lyophilized powder is reconstituted with a diluent, the viscosity can be read at 25° C. and reported at a shear rate of 1000/s, using for example, an AR-G2 cone and plate rheometer from TA Instruments of New Castle, Del. (USA). The concentration of the therapeutic protein is greater than 70 mg/mL, such as from about 140 mg/mL to about 250 mg/mL, including, for example, about 145, 160, 198, 200, 238, and 249 mg/mL. The PVP can be present at a concentration from about 0.3% to about 10%, such as from about 1%, 2%, 3%, 4%, 5%, 6%, 7%, 8%, 9%, and 10%, and increments between. The stability of the therapeutic protein is about the same when compared to a control lacking PVP; stability can be assessed by the presence of at least one selected from the group consisting of high molecular weight species, low molecular weight species, dimers, and oligomers of the therapeutic protein. In some sub-aspects, the therapeutic protein comprises at least one complementarity determining region (CDR), and can be, for example, an antibody, such as a monoclonal antibody (mAb). Furthermore, the therapeutic protein comprising at least one CDR can be an antigen-binding fragment or derivative of an antibody. The antigen binding fragment can be one selected from the group consisting of an Fab' fragment, an F'(ab)2 fragment, and an Fv fragment. In the case of a derivative of the antibody, the derivative can be selected from the group consisting of a humanized antibody, a chimeric antibody, a multi-specific antibody, a maxibody, a BiTE® molecule, a single chain antibody, a diabody, and a peptibody. The PVP has a K value of 12-17, such as 12 or 17. The PVP can have a weight average molecular weight of 11,000 Da or less, such as from about 2,000 Da to about 25,000 Da or such as from about 2,000 Da to about 3,000 Da. The composition can be formulated for delivery to a patient. The formulation can have a pH between about 4.0 to about 8.0, such as about 4.6 to about 5.4. Furthermore, the composition can comprise arginine, such as N-acetyl arginine (at a concentration of, for example, 10 mM), or a salt of arginine, such as arginine monohydrochloride (Arg HCl), arginine glutamate, or arginine acetate. In the case of Arg HCl, the Arg HCl can be present at about 67 mM. In one sub-aspect, wherein the composition comprises Arg HCL, the PVP can be present at about 1%.

In another aspect, provided herein are methods for reconstituting a lyophilized powder of the fourth aspect, comprising the step of adding a sterile aqueous diluent.

DETAILED DESCRIPTION

Figure 1:
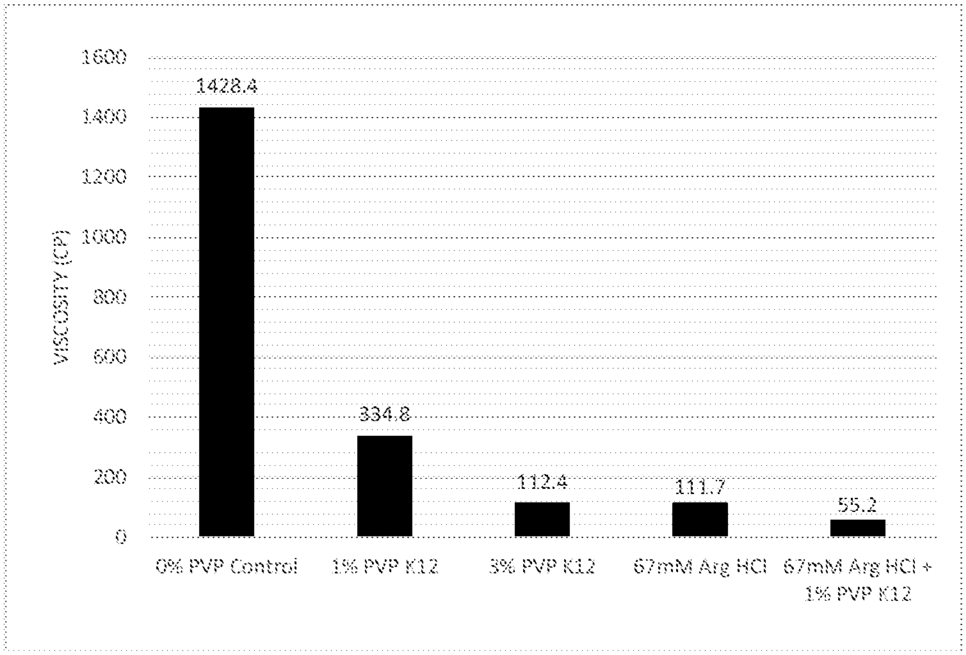
FIG. 1 shows a graph of the viscosity (in centipoise (cP)) of an IgG2 monoclonal antibody (mAb), mAb1, at a concentration of 200 mg/mL in the presence of polyvinylpyrrolidone (PVP) K12.

High concentration protein formulations often face challenges due to elevated viscosity. High viscosity formulations are difficult to handle during manufacturing, including at the bulk and filling stages. High viscosity formulations are also difficult to draw into a syringe and inject, often necessitating use of lower gauge (larger bore) needles that are unpleasant (e.g., uncomfortable or even painful) for the patient.

Disclosed herein are compositions and methods that take advantage of a surprising observation: the addition of low molecular weight polyvinylpyrrolidone (PVP) can reduce the viscosity of viscous therapeutic formulations. No commercially available PVP is sold as a viscosity reducing agent; in fact, some are sold as thickening agents (e.g., PVP K90; (2014)). PVP is sold under different trademarks, including Kollidon® (BASF), which is a trademark for a line of pharmaceutical grade of PVPs.

For example, PVP K12 and PVP K17 are low molecular weight grades that are non-toxic and acceptable for use in parenteral formulations. Both PVP K12 and PVP K17 are marketed as lyophilization agents that stabilize micro-molecular structure in lyophilisates and injectables; as dispersing agents for parenteral suspensions; and as complexing agents and dissolution enhancers, forming hydrogen bonds with compounds with complementary structures to improve dissolution (2014).

Disclosed herein are methods and compositions that take advantage of the surprising results that PVP can reduce the viscosity of high concentration therapeutic protein compositions, such as those containing antibodies (such as monoclonal antibodies (mAbs), and antigen-binding fragments thereof, as well as derivatives and analogues thereof. In some cases, PVP is combined with arginine (such as a salt of arginine, such as arginine hydrochloride, Arg-HCl), to even further decrease viscosity, a surprising result that suggests that PVP and arginine act in a complementary fashion.

Based on the results described in the Examples, PVP K12 is a preferred PVP (but not the only useful PVP) for viscosity reduction of high concentration of therapeutic proteins. For example, PVP K12 can be used at concentrations at or less than 5%; PVP K12 can be used in combination with other excipients. Interestingly, when PVP K12 and arginine-HCl are combined, a synergistic effect on viscosity reduction is observed, showing a low inherent viscosity and a low contribution to solution osmolality at concentrations tested. PVP K12 does not appear to promote therapeutic protein precipitation or induce any significant detrimental effect on protein stability at the low concentrations shown to reduce significantly viscosity.

Components of the Compositions and Methods

In the following sections, PVP (and Arg-HCl) are discussed, as are appropriate therapeutic proteins, viscosity, formulation preparation, pharmaceutical compositions, storage and kits. Other definitions can be found after the Examples.

Polyvinylpyrrolidone (PVP)

Polyvinylpyrrolidone (PVP), also known as povidone, is a synthetic polymer vehicle often used for dispersing and suspending drugs. It has multiple uses, including as a binder for tablets and capsules, a film former for ophthalmic solutions, to aid in flavoring liquids and chewable tablets, and as an adhesive for transdermal systems.

Polyvinylpyrrolidone means a molecule having the formula $(C_6H_9NO)n$, and has the structure of formula (1):

(1)

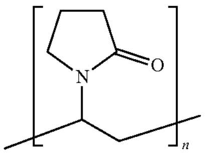

PVP, also known as povidone, polypovidone, polyvidon, polyvidonum, poly(N-vinyl-2-pyrrolidinone), poly(Nvinyl-butyrolactam), polyt 1-vinyl-2-pyrrolidinone), 1-vinyl-2-pyrrolidinone homopolymer, and poly[1-(2-oxo-l-pyrrolidinyl)ethylene]. PVP is a highly polar, amphoteric water-soluble polymer (polyamide). Purified PVP appears as a white to slightly off-white powder. PVP is often described using a k value (Fikentscher K value), which refers to the K value viscosity of the PVP. Higher K-values indicate higher K value viscosities. Commercially available PVP is available in a variety of viscosity grades according to its K value; for example, PVP K15, K30, K60, and K90; see also Table 1.

Fikentscher's value of viscosity characteristics K-value represents a viscosity index relating to molecular weight and is calculated by Fikentscher's formula (2) with relative viscosity which is measured by capillary viscometer at 25° C.:

$$K=(1.5 \log \eta_{rel}-1)/(0.15+0.003c)+(300c \log \eta_{rel}+(c+1.5c \log \eta_{rel})^2)^{1/2}/(0.15c+0.003c^2) \quad (2)$$

where $\eta_{rel}$: Relative viscosity of aqueous PVP solution to water c: Content (w/w %)of PVP in aqueous PVP solution Given that PVP is a polymer, its molecular weight can be determined via at least three different methods {Büler, 2005#12}:

1. Weight-average, expressed as Mw, where the individual weights of the molecules are determined, such as by light scattering (Table 1).
2. Number-average, expressed as Mn, and determined by methods that measure the number of molecules, such as by osmometry. This value is very seldom determined or used for PVP.
3. Viscosity-average, expressed as Mv, and determined by measuring viscosity. The value can be calculated directly from the relative viscosity, the intrinsic viscosity or the K-value (Table 1).

Polymers consist of molecules with a range of molecular weights with, in the ideal case, a Gaussian distribution {Büler, 2005 #12}.

Kollidon® is a pharmaceutical grade of PVP marketed by BASF Corporation (Florham Park, NJ). Table 1 shows the molecular weight value for Kollidon grades.

PVP can be found in the form of monomers, dimers, and polymers, and mixtures thereof.

TABLE 1

Examples of commercial pharmaceutical PVP (weight average molecular weight determined by light scattering ($M_w$); viscosity-averages values calculated from K-value range and ($M_v$) nominal K value ($M_v$) as provided in {Bühler, 2005 #12}

| Kollidon grade | $M_w$ value (Daltons)* | $M_v$ value (range) | $M_v$ value (nominal K) |
|---|---|---|---|
| Kollidon 12 | 2,000-3,000 | 2,600-5,500 | 3,900 |
| Kollidon 12 PF | 2,000-3,000 | 2,600-5,500 | 3,900 |
| Kollidon 17 PF | 7,000-11,000 | 7,100-11,000 | 9,300 |
| Kollidon 25 | 28,000-34,000 | 19,300-31,100 | 25,700 |
| Kollidon 30 | 44,000-54,000 | 31,700-51,400 | 42,500 |
| Kollidon 90 F | 1,000,000-1,500,000 | 790,000-1,350,000 | 1,100,000 |

*As determined after 1980 {Bühler, 2005 #12}

Thus, provided herein are methods for stabilizing or reducing viscosity of protein formulations (pharmaceutical formulations/pharmaceutical compositions) by adding PVP, and in some cases, Arg-HCl, in an amount effective to reduce viscosity. Also provided are reduced viscosity formulations of therapeutic proteins, including antibodies (such as monoclonal Abs (mAbs), and antigen-binding fragments thereof), containing effective amounts or concentrations of PVP, and in some cases, Arg-HCl. Also contemplated are methods of screening one or more formulations, each containing different concentrations of PVP (with and without Arg-HCl) herein to identify suitable or optimal concentrations that reduce viscosity. Further provided are methods of preparing a lyophilized powder from the disclosed reduced viscosity solution formulations, and methods of reconstituting such lyophilized powders via addition of a (sterile) diluent.

Thus, pharmaceutical formulations are provided that contain biologically active (therapeutic) polypeptides and viscosity-reducing concentrations of PVP or a combination of PVP and Arg-HCl. The reduction in viscosity is at least about 5-90% versus control formulations (e.g., lacking PVP and/or Arg-HCl). For example, the reduction in viscosity can range from about 10 to about 80%. In other cases, the reduction in viscosity is at least about 5%, 10%, 15%, 20%, 25%, 30%, 35%, 40%, 45%, 50%, 55%, 60%, 65%, 70%, 75%, 80% or 85%, or more.

The concentration and grade of PVP (with or without Arg-HCl) to reduce viscosity can be experimentally determined by one of ordinary skill. In some examples, the PVP can have a concentration from about 0.3-10%, such as (in %) about 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or 10, and any increment in between.

The weight average molecular weight ($M_w$)of the PVP, in Daltons, can be from about 2,000-25,000, such as 2,000, 2500, 3,000, 3500, 4,000, 4500, 5,000, 5500, 6,000, 6500, 7,000, 7500, 8,000, 8500, 9,000, 9500, 10,000, 10,500, 11,000, 12,000, 13,000, 14,000, 15,000, 16,000, 17,000, 18,000, 19,000, 20,000, 21,000, 22,000, 23,000, 24,000, 25,000, and any increment in-between. In some embodiments, the PVP has a weight average molecular weight, in Daltons, of less than or equal to 11,000. In other embodiments, the PVP has a weight average molecular weight that is less than or equal to 25,000 Da. In some embodiments, the PVP has a weight average molecular weight, in Daltons, of less than or equal to 20,000. In other embodiments, the PVP has a weight average molecular weight that is less than or equal to 15,000 Da. In some embodiments, the PVP has a weight average molecular weight, in Daltons, of less than or equal to 11,000. In other embodiments, the PVP has a weight average molecular weight that is less than or equal to 10,000 Da. In some embodiments, the PVP has a weight average molecular weight, in Daltons, of less than or equal to 11,000. In other embodiments, the PVP has a weight average molecular weight that is less than or equal to 10,000 Da. In yet other embodiments, the PVP has a weight average molecular weight that is less than or equal to 9,000. In other embodiments, the PVP has a weight average molecular weight equal to or less than 8,000 Da. In yet other embodiments, the PVP has a weight average molecular weight of equal to or less than 7,000 Da. In further embodiments, the PVP has a weight average molecular weight of less than or equal to 6,000 Da. In further embodiments, the PVP has a weight average molecular weight of less than or equal to 5,000 Da. In further embodiments, the PVP has a weight average molecular weight of less than or equal to 6,000 Da. In further embodiments, the PVP has a weight average molecular weight of less than or equal to 3,000 Da. And in some other embodiments, the PVP has a weight average molecular weight of less than or equal to 2,000 Da.

Expressed as viscosity-average values of the molecular weight, $M_v$, calculated from the K value, of the PVP, in Daltons, can be from about 2600-25,000, such as from about 2,600 to about 5,500 (K12) (including the $M_v$ calculated from the nominal K value of 3900) and from about 7100 to about 11,000 (K17) (including the $M_v$ calculated from the nominal K value of 9300), as well as from about 11,000 to about 25,000. For example, the viscosity-average value of the molecular weight can be 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 6000, 7000, 7100, 7500, 8000, 8500, 9000, 9500, 10,000, 10,500, 11,000, 12,000, 13,000, 14,000, 15,000, 16,000, 17,000, 18,000, 19,000, 20,000, 21,000, 22,000, 23,000, 24,000, 25,000, and any increment in-between. In some embodiments, the PVP has a weight average molecular weight, in Daltons, of less than or equal to 11,000. In other embodiments, the PVP has a weight average molecular weight that is less than or equal to 25,000 Da. In some embodiments, the PVP has a weight average molecular weight, in Daltons, of less than or equal to 20,000. In other embodiments, the PVP has a weight average molecular weight that is less than or equal to 15,000 Da. In some embodiments, the PVP has a weight average molecular weight, in Daltons, of less than or equal to 11,000. In other embodiments, the PVP has a weight average molecular weight that is less than or equal to 10,000 Da. In yet other embodiments, the PVP has a weight average molecular weight that is less than or equal to 9,000. In other embodiments, the PVP has a weight average molecular weight equal to or less than 8,000 Da. In yet other embodiments, the PVP has a weight average molecular weight of equal to or less than 7,000 Da. In further embodiments, the PVP has a weight average molecular weight of less than or equal to 6,000 Da. In further embodiments, the PVP has a weight average molecular weight of less than or equal to 5,000 Da. In further embodiments, the PVP has a weight average molecular weight of less than or equal to 6,000 Da. In further embodiments, the PVP has a weight average molecular weight of less than or equal to 3,000 Da. And in some other embodiments, the PVP has a weight average molecular weight of less than or equal to 2,600 Da.

In some embodiments, arginine is present. In some embodiments, the arginine is present as a salt of arginine. In some embodiments, the arginine salt is Arg-HCl. In such embodiments, the concentration of Arg-HCl can vary, from about 0.1 mM to about 100 mM, including, for example, (in mM) about 0.1, 0.25, 0.5, 0.75, 1, 2, 3, 4, 5, 6, 7, 8, 9, 10, 12.5, 15, 17.5, 20, 22.5, 25, 27.5, 30, 35, 40, 45, 50, 55, 60, 65, 70, 75, 80,.85, 90, 95, and 100 in increments in between; the concentration of Arg-HCl can also be, in mM, 110, 120, 125, 130, 140, 150, 160, 170, 175, 180, 190, and 200; and increments in between. The arginine salt can also be Arg acetate or Arg glutamate and is present at a concentration of about 25 mM to about 150 mM, such as about 25, 30, 35, 40, 45, 50, 55, 60, 65, 70, 75, 80, 85, 90, 95, 100, 105, 110, 115, 120, 125, 130, 135, 140, 145, or about 150 mM. With or without a salt of arginine, N-acetyl arginine can also be present at a concentration of about 25 mM to about 230 mM, such as about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, or about 230 mM and an increment therebetween.

Therapeutic Polypeptides

Exemplary protein concentrations in the formulation can range from about 70 mg/ml to about 300 mg/ml, about 120 mg/ml to about 270 mg/ml, from about 140 mg/ml to about 255 mg/ml, from about 140 mg/ml to about 240 mg/ml, or from about 140 mg/ml to about 220 mg/ml, or alternatively from about 190 mg/ml to about 210 mg/ml. The concentration of protein depends upon the end use of the pharmaceutical formulation and can be easily determined by a person of skill in the art. Particularly contemplated concentrations of protein are at least about 70, 75, 80, 85, 90, 95, 100, 105, 110, 115, 120, 125, 130, 135, 140, 145, 150, 155, 160, 165, 170, 175, 180, 185, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, and 300 mg/ml.

Viscosity and Other Characteristics of the PVP-Containing Formulations

In one aspect, the disclosed pharmaceutical formulations (with PVP, and with or without Arg-HCl) have a viscosity level of less than about 80 centipoise (cP) as measured at room temperature (i.e., 25° C.). In certain embodiments, the pharmaceutical formulation has a viscosity level of less than about 80 cP to less than about 1 cP, such as 80 cP, 70 cP, about 60 cP, about 50 cP, about 40 cP, about 30 cP, about 25 cP, about 20 cP, about 18 cP, about 15 cP, about 12 cP, about 10 cP; about 8 cP, about 6 cP, about 4 cP; about 2 cP; or about 1 cP.

In one aspect, the pharmaceutical formulation is stable as measured by at least one stability assay, such as an assay that examines the biophysical or biochemical characteristics of the therapeutic protein (such as an antibody) over time. A stable pharmaceutical formulation" or "stable formulation" refers to a pharmaceutical formulation of comprising a therapeutic protein that exhibits limited increased aggregation and/or reduced loss of biological activity of not more than 5%-10% when stored at about −30° C. (or colder) to about 5° C. to about 40° C. for at least one month, or two months, or three months, or six months, or one year, or two years, or five years, or longer when compared to a control formulation sample. Formulation stability can be determined using any number of standard assays, including size-exclusion HPLC (SEC-HPLC), cation-exchange HPLC (CEX-HPLC), Subvisible Particle Detection by Light Obscuration ("HIAC") and/or visual inspection. Typically, the warmer the storage temperature, the shorter the shelf-life of the formulation.

Pharmaceutical formulation stability can also be assessed using visual assessment. Visual assessment is a qualitative method used to describe the visible physical characteristics of a sample. The sample is viewed against a black and/or white background of an inspection booth, depending on the characteristic being evaluated (e.g., color, clarity, presence of particles or foreign matter). Samples are also viewed against an opalescent reference standard and color reference standards. In the case of visual assessment, a stable pharmaceutical formulation exhibits no significant change in color, clarity, presence of particles or foreign matter as compared to a control sample.

Formulations can have any pH that at once is appropriate for the therapeutic polypeptide to maintain activity and acceptable stability, as well as being suitable for administration to a patient. For example, pH can be from about 4.0 to about 8.0, such as about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, and 8.0. In some cases, the pH range is from about 4.6 to about 5.4

Pharmaceutical Composition Formulation and Components

Pharmaceutical compositions, suitable for administration to a patient, can be prepared not only with PVP (and in some cases, with arginine, such as Arg HCl), but formulated with other components.

Acceptable pharmaceutical components preferably are nontoxic to patients at the dosages and concentrations used. Pharmaceutical compositions can comprise agents for modifying, maintaining or preserving, for example, the pH, osmolarity, viscosity, clarity, color, isotonicity, odor, sterility, stability, rate of dissolution or release, adsorption or penetration of the composition.

In general, excipients can be classified on the basis of the mechanisms by which they stabilize proteins against various chemical and physical stresses. Some excipients alleviate the effects of a specific stress or regulate a particular susceptibility of a specific polypeptide. Other excipients more generally affect the physical and covalent stabilities of proteins.

Common excipients of liquid and lyophilized protein formulations are shown in Table A (see also (Kamerzell et al 2011).

TABLE A

Examples of excipient components for polypeptides formulations

| Component | Function | Examples |
|---|---|---|
| Buffers | Maintaining solution pH<br>Mediating buffer-ion specific interactions with polypeptides | Citrate, Succinate, Acetate, Glutamate, Aspartate, Histidine, Phosphate, Tris, Glycine |
| Sugars and carbohydrates | Stabilizing polypeptides<br>Tonicifying agents<br>Acting as carriers for inhaled drugs (e.g., lactose)<br>Providing dextrose solutions during IV administration | Sucrose, Trehalose, Sorbitol, Mannitol, Glucose, Lactose, Cyclodextrin derivatives |
| Stabilizers and bulking agents | Enhancing product elegance and preventing blowout<br>Providing structural strength to a lyo cake | Mannitol, Glycine |
| Osmolytes | Stabilizing against environmental stress (temperature, dehydration) | Sucrose, Trehalose, Sorbitol, Glycine, Proline, Glutamate, Glycerol, Urea |

TABLE A-continued

| Examples of excipient components for polypeptides formulations | | |
|---|---|---|
| Component | Function | Examples |
| Amino acids | Mediating specific interactions with polypeptides<br>Providing antioxidant activity (e.g., His, Met)<br>Buffering, tonicifying | Histidine, Arginine, Glycine, Proline, Lysine, Methionine, Amino acid mixtures (e.g., Glu/Arg) |
| Polypeptides and polymers | Acting as competitive inhibitors of polypeptide adsorption<br>Providing bulking agents for lyophilization<br>Acting as drug delivery vehicles | HSA, PVA, PVP, PLGA, PEG, Gelatin, Dextran, Hydroxyethyl starch, HEC, CMC |
| Anti-oxidants | Preventing oxidative polypeptides damage<br>Metal ion binders (if a metal is included as a cofactor or is required for protease activity)<br>Free radical scavengers | Reducing agents, Oxygen scavengers, Free radical scavengers, Chelating agents (e.g., EDTA, EGTA, DTPA), Ethanol |
| Metal ions | Polypeptides cofactors<br>Coordination complexes (suspensions) | Magnesium, Zinc |
| Specific ligands | Stabilizers of native conformation against stress-induced unfolding<br>Providing conformation flexibility | Metals, Ligands, Amino acids, Polyanions |
| Surfactants | Acting as competitive inhibitors of polypeptides adsorption<br>Acting as competitive inhibitor of polypeptides surface denaturation<br>Providing liposomes as drug delivery vehicles<br>Inhibiting aggregation during lyophilization<br>Acting as reducer of reconstitution times of lyophilized products | Polysorbate 20, Polysorbate 80, Poloxamer 188, Anionic surfactants (e.g., sulfonates and sulfosuccinates), Cationic surfactants, Zwitterionic surfactants |
| Salts | Tonicifying agents<br>Stabilizing or destabilizing agents for polypeptides, especially anions | NaCl, KCl, $NaSO_4$ |
| Preservatives | Protecting against microbial growth | Benzyl alcohol, M-cresol, Phenol |

Other excipients are known in the art (e.g., see (Powell et al 1998))(Powell et al 1998). Those skilled in the art can determine what amount or range of excipient can be included in any particular formulation to achieve a biopharmaceutical composition that promotes retention in stability of the biopharmaceutical. For example, the amount and type of a salt to be included in a biopharmaceutical composition can be selected based on to the desired osmolality (i.e., isotonic, hypotonic or hypertonic) of the final solution as well as the amounts and osmolality of other components to be included in the formulation.

Polypeptide Formulation Preparation

Pharmaceutical formulations disclosed herein can be prepared by either of two processes designated processes 1 and 2. Process 1 comprises:

a. dialyzing or concentrating a solution of a therapeutic protein;
b. dialyzing or concentrating a solution of selected excipients or providing a dry mixture of selected excipients;
c. adding the excipient solution or the dry excipient mixture into the protein solution at a selected pH to achieve a desired final excipient concentration, a desired final protein concentration, and a desired final pH.
d. UF/DF ultra-filtration diafiltration process exchanges the buffer and concentrates the protein simultaneously.

Process 2 comprises:

a. dialyzing a solution of therapeutic protein;
b. dialyzing a solution of selected excipients or providing a dry mixture of selected excipients;
c. adding the excipient solution or dry excipient mixture into the dialyzed protein solution at a selected pH and a desired excipient concentration, and
d. concentrating the solution resulting from step c to a desired final protein concentration and desired final pH In process 1, the pH of the concentrated protein to achieve the desired final pH can range from about 4 to about 8. In process 2, the pH of the concentrated protein solution to achieve the desired final pH can range from about 4 to about 8. Where a particular excipient is reported in a formulation by, for example, percent (%) w/v, those skilled in the art recognize that the equivalent molar concentration of that excipient is also contemplated.

The formulations can be lyophilized for later resuspension with an appropriate diluent; often liquid formulations are modified to incorporate a cryoprotectant and a bulking agent; acetates are substituted with glutamates or phosphates to reduce volatility.

Storage and Kits

Once the pharmaceutical formulation has been formulated, it can be stored in sterile vials as a solution, suspension, gel, emulsion, solid, or as a dehydrated or lyophilized powder. Such formulations can be stored either in a ready-to-use form or in a form (e.g., lyophilized) that is reconstituted prior to administration. In some cases, the therapeutic polypeptide formulations can be stored in containers, such as suitable storage bags (e.g., as manufactured by Sartorius (Gottingen, DE)) or in polycarbonate carboys. Once the pharmaceutical formulation has been formulated, it can also be stored in pre-filled syringes (PFS; such as 2.25 ml PFS's) as a solution or suspension in a ready-to-use form, as well as in glass vials (such as 5 cc glass vials).

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

Embodiments

Embodiment 1: A composition comprising a concentration of a therapeutic protein and polyvinylpyrrolidone (PVP), wherein the viscosity of the composition comprising the PVP is less than a composition comprising the same concentration of the therapeutic protein, but the PVP is absent.

Embodiment 2: A composition comprising a concentration of a therapeutic protein and PVP, wherein the viscosity of the composition is less than or equal to 80 cP.

Embodiment 3: The composition of embodiment 2, wherein the viscosity of the composition is less than or equal to 70 cP.

Embodiment 4: The composition of embodiment 2, wherein the viscosity of the composition is less than or equal to 40 cP.

Embodiment 5: The composition of embodiment 2, wherein the viscosity of the composition is less than or equal to 20 cP.

Embodiment 6: The composition of embodiment 1 or 2, wherein the viscosity of the composition is read at 25° C. and reported at a shear rate of 1000/s.

Embodiment 7: The composition of embodiment 6, wherein the viscosity is measured using an AR-G2 cone and plate rheometer from TA Instruments of New Castle, Delaware (USA).

Embodiment 8: The composition of embodiment 1 or 2, wherein the concentration of the therapeutic protein is greater than 70 mg/mL.

Embodiment 9: The composition of embodiment 8, wherein the concentration of the therapeutic protein is greater than or equal to about 140 mg/mL to about 250 mg/mL.

Embodiment 10: The composition of embodiment 9, wherein the concentration of the therapeutic protein, in mg/mL, is selected from the group consisting of about 145, 160, 198, 200, 238, and 249.

Embodiment 11: The composition of embodiment 1 or 2, wherein the PVP is present at a concentration from about 0.3% to about 10%.

Embodiment 12: The composition of embodiment 11, wherein the PVP is present at a concentration selected from the group consisting of about 1%, 2%, 3%, 4%, 5%, 6%, 7%, 8%, 9%, and 10%, and increments between.

Embodiment 13: The composition of embodiment 1 or 2, wherein stability of the therapeutic protein is about the same when compared to a control lacking PVP.

Embodiment 14: The composition of embodiment 13, wherein stability is assessed by the presence of at least one selected from the group consisting of high molecular weight species, low molecular weight species, dimers, and oligomers.

Embodiment 15: The composition of embodiment 1 or 2, wherein the therapeutic protein comprises at least one complementarity determining region (CDR).

Embodiment 16: The composition of embodiment 15, wherein the therapeutic protein is an antibody.

Embodiment 17: The composition of embodiment 16, wherein the antibody is a monoclonal antibody (mAb).

Embodiment 18: The composition of embodiment 17, wherein the antibody is an antigen-binding fragment or derivative of the antibody.

Embodiment 19: The composition of embodiment 18, wherein the antigen binding fragment is selected from the group consisting of an Fab' fragment, an F'(ab)2 fragment, and an Fv fragment.

Embodiment 20: The composition of embodiment 18, wherein the derivative of the antibody is selected from the group consisting of a humanized antibody, a chimeric antibody, a multi-specific antibody, a maxibody, a BiTE® molecule, a single chain antibody, a diabody, and a peptibody.

Embodiment 21: The composition of embodiment 1 or 2, wherein the PVP has a K value of 12-17, such as 12 or 17.

Embodiment 22: The composition of embodiment 1 or 2, wherein the PVP has a weight average molecular weight of 11,000 Da or less.

Embodiment 23: The composition of embodiment 23, wherein the PVP has a weight average molecular weight of from about 2,000 Da to about 25,000 Da.

Embodiment 24: The composition of embodiment 24, wherein the PVP has a weight average molecular weight of from about 2,000 Da to about 3,000 Da.

Embodiment 25: The composition of embodiment 1 or 2, wherein the composition is formulated for delivery to a patient.

Embodiment 26: The composition of embodiment 1 or 2, having a pH between about 4.0 to about 8.0.

Embodiment 27: The composition of embodiment 26, having a pH of about 4.6 to about 5.4.

Embodiment 28: The composition of embodiment 1 or 2, further comprising arginine.

Embodiment 29: The composition of embodiment 28, wherein the arginine is N-acetyl arginine.

Embodiment 30: The composition of embodiment 29, wherein the N-acetyl arginine is present at about 10 mM.

Embodiment 31: The composition of embodiment 28, wherein the arginine is a salt of arginine.

Embodiment 32: The composition of embodiment 31, wherein the arginine is arginine monohydrochloride (Arg HCl), arginine glutamate, or arginine acetate.

Embodiment 33: The composition of embodiment 32, wherein the Arg HCl is present at about 67 mM.

Embodiment 34: The composition of embodiment 33, wherein the PVP is present at about 1%.

Embodiment 35: A method of preparing a lyophilized powder comprising the step of lyophilizing the composition of embodiments 1 or 2.

Embodiment 36: A method of reducing the viscosity of a pharmaceutical formulation comprising a therapeutic protein, comprising the step of combining the therapeutic protein with a viscosity-reducing concentration of PVP.

Embodiment 37: The method of embodiment 36, wherein the viscosity of the composition is less than or equal to 80 cP.

Embodiment 38: The method of embodiment 36, wherein the viscosity of the composition is less than or equal to 70 cP.

Embodiment 39: The method of embodiment 36, wherein the viscosity of the composition is less than or equal to 40 cP.

Embodiment 40: The method of embodiment 36, wherein the viscosity of the composition is less than or equal to 20 cP.

Embodiment 41: The method of embodiment 36, wherein the viscosity of the composition is read at 25° C. and reported at a shear rate of 1000/s.

Embodiment 42: The method of embodiment 42, wherein the viscosity is measured using an AR-G2 cone and plate rheometer from TA Instruments of New Castle, Del. (USA).

Embodiment 43: The method of embodiment 36, wherein the concentration of the therapeutic protein is greater than 70 mg/mL.

Embodiment 44: The method of embodiment 43, wherein the concentration of the therapeutic protein is greater than or equal to about 140 mg/mL to about 250 mg/mL.

Embodiment 45: The method of embodiment 44, wherein the concentration of the therapeutic protein, in mg/mL, is selected from the group consisting of about 145, 160, 198, 200, 238, and 249.

Embodiment 46: The method of embodiment 36, wherein the PVP is present at a concentration from about 0.3% to about 10%.

Embodiment 47: The method of embodiment 46, wherein the PVP is present at a concentration selected from the group consisting of about 1%, 2%, 3%, 4%, 5%, 6%, 7%, 8%, 9%, and 10%, and increments between.

Embodiment 48: The method of embodiment 36, wherein stability of the therapeutic protein is about the same when compared to a control lacking PVP.

Embodiment 49: The method of embodiment 48, wherein stability is assessed by the presence of at least one selected from the group consisting of high molecular weight species, low molecular weight species, dimers, and oligomers.

Embodiment 50: The method of embodiment 36, wherein the therapeutic protein comprises at least one complementarity determining region (CDR).

Embodiment 51: The method of embodiment 50, wherein the therapeutic protein is an antibody.

Embodiment 52: The method of embodiment 51, wherein the antibody is a monoclonal antibody (mAb).

Embodiment 53: The method of embodiment 51, wherein the antibody is an antigen-binding fragment or derivative of the antibody.

Embodiment 54: The method of embodiment 53, wherein the antigen binding fragment is selected from the group consisting of an Fab' fragment, an F'(ab)2 fragment, and an Fv fragment.

Embodiment 55: The method of embodiment 53, wherein the derivative of the antibody is selected from the group consisting of a humanized antibody, a chimeric antibody, a multi-specific antibody, a maxibody, a BiTE® molecule, a single chain antibody, a diabody, and a peptibody.

Embodiment 56: The method of embodiment 36, wherein the PVP has a K value of 12-17, such as 12 or 17.

Embodiment 57: The method of embodiment 36, wherein the PVP has a weight average molecular weight of 11,000 Da or less.

Embodiment 58: The method of embodiment 57, wherein the PVP has a weight average molecular weight of from about 2,000 Da to about 25,000 Da.

Embodiment 59: The method of embodiment 58, wherein the PVP has a weight average molecular weight of from about 2,000 Da to about 3,000 Da.

Embodiment 60: The method of embodiment 36, wherein the composition is formulated for delivery to a patient.

Embodiment 61: The method of embodiment 36, wherein the composition has a pH between about 4.0 to about 8.0 after reconstitution with a diluent.

Embodiment 62: The method of embodiment 61, wherein the composition has a pH of about 4.6 to about 5.4.

Embodiment 63: The method of embodiment 33, wherein the composition further comprises arginine.

Embodiment 64: The method of embodiment 64, wherein the arginine is N-acetyl arginine.

Embodiment 65: The method of embodiment 65, wherein the N-acetyl arginine is present at about 10 mM.

Embodiment 66: The method of embodiment 63, wherein the arginine is a salt of arginine.

Embodiment 67: The method of embodiment 66, wherein the arginine is arginine monohydrochloride (Arg HCl), arginine glutamate, or arginine acetate.

Embodiment 68: The method of embodiment 67, wherein the Arg HCl is present at about 67 mM.

Embodiment 69: The method of embodiment 68, wherein the PVP is present at about 1%.

Embodiment 70: A lyophilized powder comprising a therapeutic protein and PVP, wherein the PVP is present at a weight:weight concentration effective to reduce viscosity after reconstitution with a diluent.

Embodiment 71: The lyophilized powder of embodiment 70, wherein the PVP is present at a concentration of between about 100 μg/mg therapeutic protein to about 1 mg/mg therapeutic protein.

Embodiment 72: The lyophilized powder of embodiment 71, wherein the PVP is present at a concentration between about 200 μg/mg to about 500 μg/mg therapeutic protein to about 1 mg/mg therapeutic protein before reconstitution with a diluent.

Embodiment 73: The lyophilized powder of embodiment 71, wherein the viscosity of the method is less than or equal to 80 cP after reconstitution with a diluent.

Embodiment 74: The lyophilized powder of embodiment 71, wherein the viscosity of the method is less than or equal to 70 cP after reconstitution with a diluent.

Embodiment 75: The lyophilized powder of embodiment 71, wherein the viscosity of the method is less than or equal to 40 cP after reconstitution with a diluent.

Embodiment 76: The lyophilized powder of embodiment 71, wherein the viscosity of the method is less than or equal to 20 cP after reconstitution with a diluent.

Embodiment 77: The lyophilized powder of embodiment 71, wherein the viscosity of the method is read at 25 ° C. and reported at a shear rate of 1000/s after reconstitution with a diluent.

Embodiment 78: The lyophilized powder of embodiment 71, wherein the viscosity is measured using an AR-G2 cone and plate rheometer from TA Instruments of New Castle, Del. (USA).

Embodiment 79: The lyophilized powder of embodiment 70, wherein the PVP is present at a concentration from about 0.3% to about 10% after reconstitution with a diluent.

Embodiment 80: The lyophilized powder of embodiment 79, wherein the PVP is present at a concentration selected from the group consisting of about 1%, 2%, 3%, 4%, 5%, 6%, 7%, 8%, 9%, and 10%, and increments between after reconstitution with a diluent.

Embodiment 81: The lyophilized powder of embodiment 70, wherein the therapeutic protein comprises at least one complementarity determining region (CDR).

Embodiment 82: The lyophilized powder of embodiment 81, wherein the therapeutic protein is an antibody.

Embodiment 83: The lyophilized powder of embodiment 82, wherein the antibody is a monoclonal antibody (mAb).

Embodiment 84: The lyophilized powder of embodiment 82, wherein the antibody is an antigen-binding fragment or derivative of the antibody.

Embodiment 85: The lyophilized powder of embodiment 84, wherein the antigen binding fragment is selected from the group consisting of an Fab' fragment, an F'(ab)2 fragment, and an Fv fragment.

Embodiment 86: The lyophilized powder of embodiment 85, wherein the derivative of the antibody is selected from the group consisting of a humanized antibody, a chimeric antibody, a multi-specific antibody, a maxibody, a BiTE® molecule, a single chain antibody, a diabody, and a peptibody.

Embodiment 87: The lyophilized powder of embodiment 70, wherein the PVP has a K value of 12-17, such as 12 or 17.

Embodiment 88: The lyophilized powder of embodiment 70, wherein the PVP has a weight average molecular weight of 11,000 Da or less.

Embodiment 89: The lyophilized powder of embodiment 88, wherein the PVP has a weight average molecular weight of from about 2,000 Da to about 25,000 Da.

Embodiment 90: The lyophilized powder of embodiment 89, wherein the PVP has a weight average molecular weight of from about 2,000 Da to about 3,000 Da.

Embodiment 91: The lyophilized powder of embodiment 70, wherein the method is formulated for delivery to a patient after reconstitution with a diluent.

Embodiment 92: The lyophilized powder of embodiment 70, having a pH between about 4.0 to about 8.0 after reconstitution with a diluent.

Embodiment 93: The lyophilized powder of embodiment 92, having a pH of about 4.6 to about 5.4.

Embodiment 94: The lyophilized powder of embodiment 70, further comprising arginine.

Embodiment 95: The lyophilized powder of embodiment 94, wherein the arginine is N-acetyl arginine.

Embodiment 96: The lyophilized powder of embodiment 95, wherein the N-acetyl arginine is present at about 10 mM.

Embodiment 97: The lyophilized powder of embodiment 94, wherein the arginine is a salt of arginine.

Embodiment 98: The lyophilized powder of embodiment 97, wherein the arginine is arginine monohydrochloride (Arg HCl), arginine glutamate, or arginine acetate.

Embodiment 99: The lyophilized powder of embodiment 98, wherein the arginine hydrochloride is present at about 67 mM.

Embodiment 100: The lyophilized powder of embodiment 99, wherein the PVP is present at about 1%.

Embodiment 101: A method for reconstituting a lyophilized powder of embodiment 70, comprising the step of adding a sterile aqueous diluent.

The following Examples are given solely by way of example and are not set forth to limit the disclosure or claims in any way.

EXAMPLES

Example 1—PVP K12 as a Viscosity-Reducing Excipient (with and without Arginine-HCl) in a High Concentration of mAb Solution (mAb1)

To assess the impact of PVP K12 on viscosity of a high concentration of a therapeutic mAb (IgG2), mAb1. mAb1 was dialyzed against 15 mM sodium acetate pH 5.2. Following dialysis, mAb1 was concentrated to 220 mg/mL using Amicon® Ultra 10K molecular weight cut-off (MWCO) centrifugal filters (Millipore Sigma; Burlington, Mass.). Concentrated excipient stock solutions (PVP K12 (BASF Corp. (headquartered in Ludwigshafen, Germany); and arginine HCl (Sigma-Aldrich; St. Louis, Mo.) were then spiked into this material at 10% volume, diluting the mAb1 concentration to 200 mg/mL. The viscosity of each sample was measured using an AR-G2 cone and plate rheometer (TA Instruments; New Castle, Del) at 25° C. with data reported at a shear rate of 1000/s. Data in FIG. 1 show that 1% and 3% PVP K12 addition resulted in a substantial decrease in mAb1 formulation viscosity. The amount of reduction for 3% PVP K12 is comparable to the level seen with the addition of 67 mM arginine HCl (Arg-HCl), which was used for comparison. The combination of 1% PVP K12 with 67 mM arginine HCl unexpectedly showed further reduction in viscosity compared to the formulations containing a single excipient.

Example 2—PVP K12 as a Viscosity-Reducing Excipient (with and without Arginine-HCl) in a High Concentration of mAb Solution (mAb2)

Figure 2:
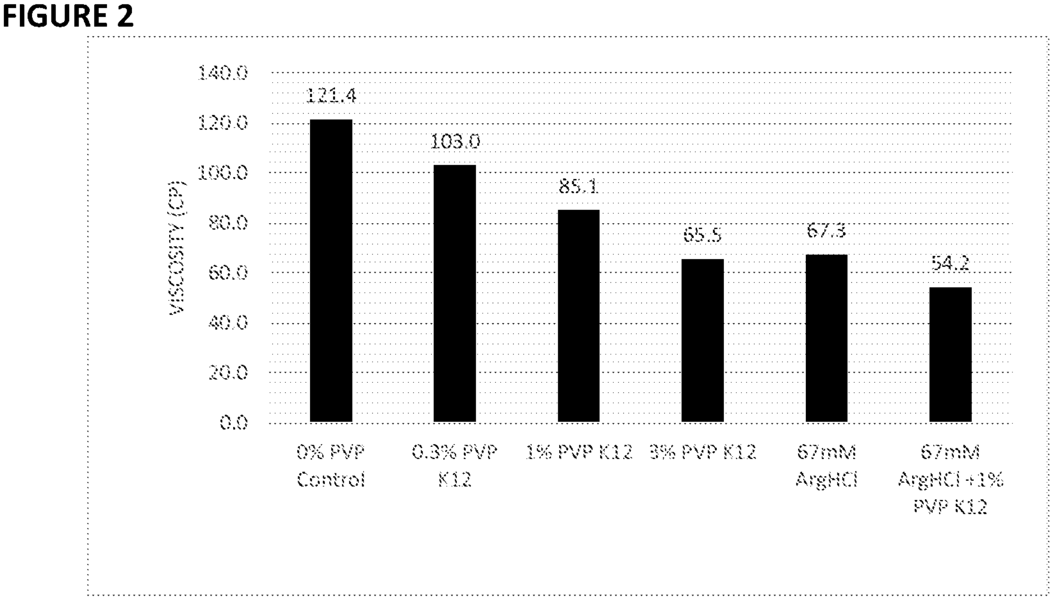
FIG. 2 shows a graph of the effect of PVP K12 on viscosity of solutions of mAb2, a therapeutic IgG1 mAb, at a concentration of 198 mg/mL.

An experiment was performed to assess the impact of PVP K12 on the viscosity of a high concentration of a therapeutic mAb, mAb2 (IgG1). mAb2 was dialyzed against 10 mM sodium acetate pH 5.2 containing 10 mM N-acetyl arginine (NAR). Following dialysis, mAb2 was concentrated to 220 mg/mL using Amicon Ultra 10K MWCO centrifugal filters. Concentrated excipient stock solutions were then spiked into this material at 10% volume, diluting the mAb2 concentration to 198 mg/mL. Viscosities of the samples were measured using an AR-G2 cone and plate rheometer at 25 ° C. with data reported at a shear rate of 1000/s. Data in FIG. 2 show that 0.3%, 1%, and 3% PVP K12 addition (in the presence of 10 mM NAR) resulted in a decrease in mAb2 formulation viscosity, with the 3% PVP formulation having the lowest viscosity among the three PVP concentrations tested. The amount of reduction for 3% PVP K12 was comparable to the level seen with the addition of 67 mM Arginine HCl, which was included for comparison. The combination of 1% PVP K12 with 67 mM Arginine HCl unexpectedly showed further reduction in viscosity compared to the formulations containing a single excipient.

Example 3—PVP K12 as a Viscosity-Reducing Excipient (with and without Arginine-HCl) in a High Concentration of mAb Solution (mAb3)

Figure 3:
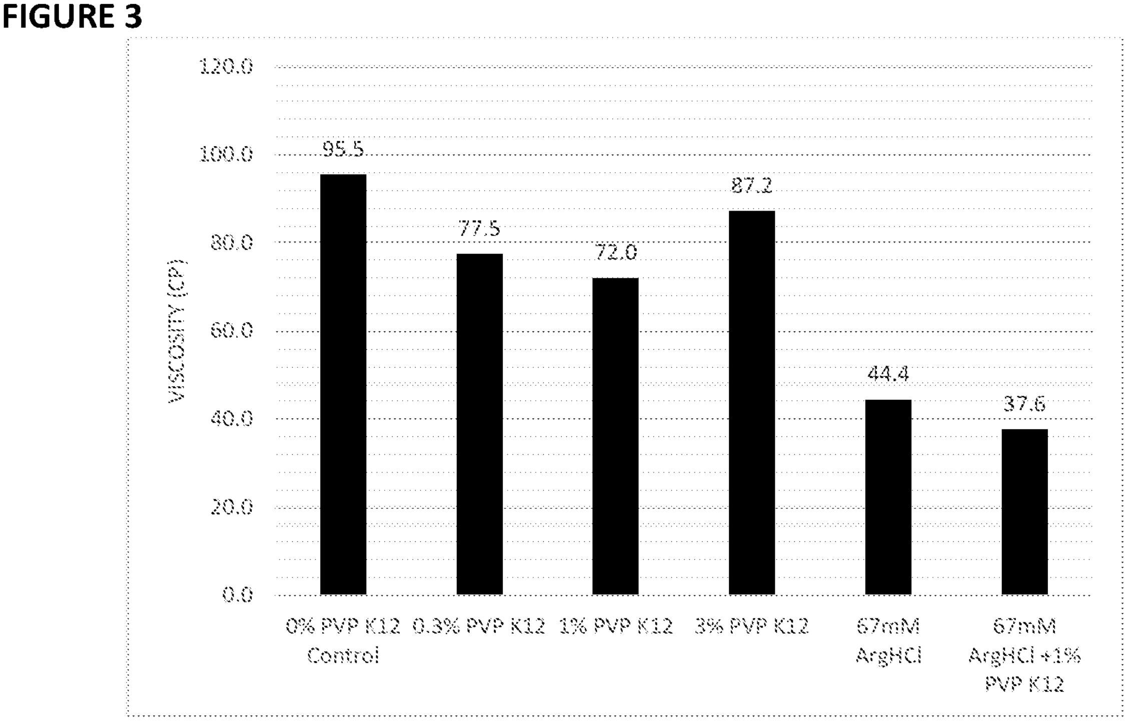
FIG. 3 shows a graph of the effect of PVP K12 on viscosity of solutions of mAb3, a therapeutic IgG1 mAb, at a concentration of 238 mg/mL.

An experiment was performed to assess the impact of PVP K12 on the viscosity of a high concentration of a therapeutic mAb, mAb3 (IgG1). mAb3 was dialyzed against 15 mM sodium acetate pH 5.2. Following dialysis, mAb3 was concentrated to 265 mg/mL using Amicon Ultra 10K MWCO centrifugal filters. Concentrated excipient stock solutions were then spiked into this material at 10% volume, diluting the mAb3 concentration to 238 mg/mL. Viscosities of the samples were measured using an AR-G2 cone and plate rheometer at 25° C. with data reported at a shear rate of 1000/s. Data in FIG. 3 Error! Reference source not found. show that 0.3%, 1%, and 3% PVP K12 addition resulted in a decrease in mAb3 formulation viscosity with the 1% PVP K12 formulation having the lowest viscosity among the three PVP concentrations tested. The combination of 1% PVP K12 with 67 mM Arginine HCl unexpectedly showed further reduction in viscosity compared to the formulations containing a single excipient.

Example 4—PVP K12 as a Viscosity-Reducing Excipient (with and without Arginine-HCl) in a High Concentration of mAb Solution (mAb4)

An experiment was performed to assess the impact of PVP K12 on the viscosity of a therapeutic mAb, mAb4

Figure 4:
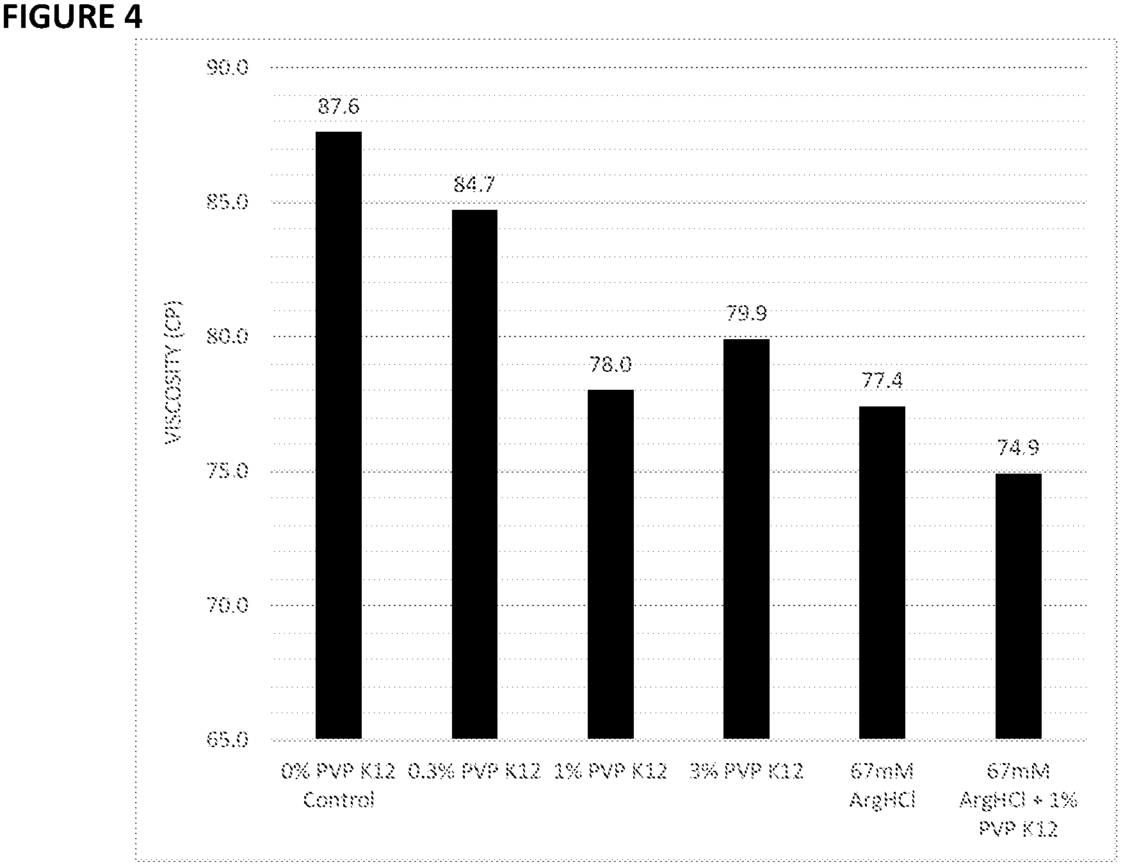
FIG. 4 shows a graph of the effect of PVP K12 on viscosity of solutions of mAb4, a therapeutic IgG1 mAb, at a concentration of 249 mg/mL.

(IgG1). mAb4 was dialyzed against 15 mM sodium acetate pH 5.2. Following dialysis, mAb3 was concentrated to 277 mg/mL using Amicon Ultra 10K MWCO centrifugal filters. Concentrated excipient stock solutions were then spiked into this material at 10% volume, diluting the mAb4 concentration to 249 mg/mL. Viscosities of the samples were measured using an ARG2 cone and plate rheometer at 25° C. with data reported at a shear rate of 1000/ s. Data in FIG. 4 show that 0.3%, 1%, and 3% PVP K12 addition result in a decrease in mAb4 formulation viscosity with the 1% PVP formulation having the lowest viscosity among the three PVP concentrations tested. The amount of reduction for 1% PVP K12 was comparable to the level seen with the addition of 67 mM Arginine HCl, which was included for comparison. The combination of 1% PVP K12 with 67 mM Arginine HCl unexpectedly showed further reduction in viscosity compared to the formulations containing a single excipient.

Example 5—Effect of Different PVP K12 Concentration in High Concentration of mAb Solutions (mAb1)

Figure 5:
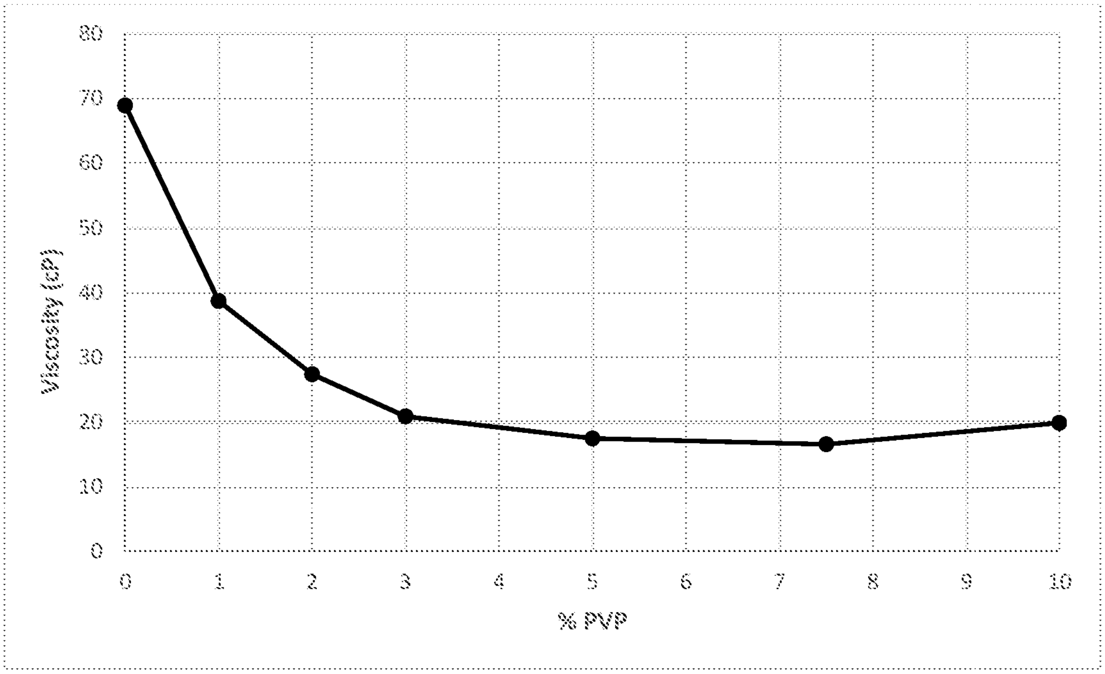
FIG. 5 shows a graph of the effect of PVP K12 concentrations on the viscosity of mAb1 at a concentration of 145 mg/mL.

An experiment was performed to assess the effect of different concentrations of PVP K12 on the reduction of mAb1 formulation viscosity. mAb1 was dialyzed against 15 mM sodium acetate pH 5.2 and concentrated to 181 mg/mL using Amicon Ultra 10K MWCO centrifugal filters. A 50% (w/v) solution of PVP K12 was then spiked into the concentrated protein solutions to generate a range of PVP concentrations up to 10%. Final mAb concentration was 145 mg/mL. Viscosities of the samples were measured using an AR-G2 cone and plate rheometer at 25° C. with data reported at a shear rate of 1000/s. The data in FIG. 5 show that as PVP K12 concentration increases, viscosity-lowering begins to diminish when PVP K12 concentration 3%. Minimum viscosity was achieved between 5% and 10% PVP K12 with viscosity increasing between 7.5% and 10% PVP K12.

Example 6—Comparing Effects on Viscosity Using Varying Molecular Weight PVP in a High Concentration mAb Solution (mAb1)

Figure 6:
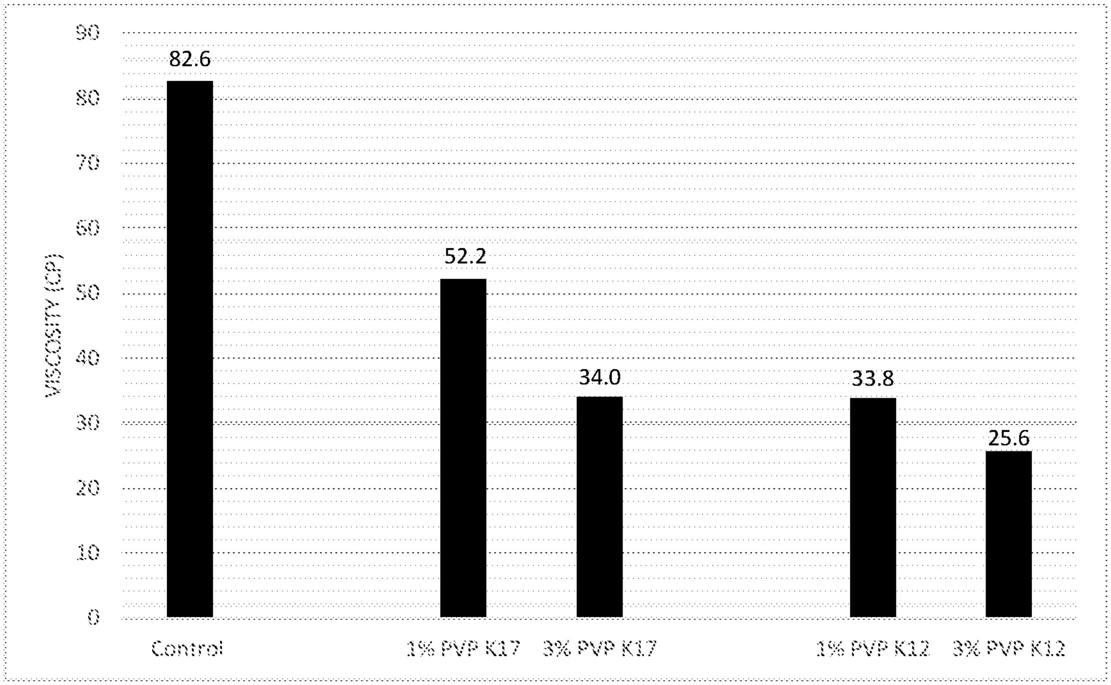
FIG. 6 shows a graph comparing the viscosity effects of PVP having two different molecular weights on solutions having a high concentration (160 mg/mL) of mAb1.

An experiment was performed to compare the effects of PVP of varying molecular weights on viscosity of mAb1 formulations. mAb1 was dialyzed against 15 mM sodium acetate pH 5.2. Following dialysis, mAb1 was concentrated to 178 mg/mL using Amicon Ultra 10K MWCO centrifugal filters. Concentrated excipient stock solutions of PVP K12 (MW: 2,000-3,000 Da) and PVP K17 (MW: 7,000-11,000 Da) (all from BASF Corp.) were then spiked into this material at 10% volume, diluting the mAb1 concentration to 160 mg/mL. Viscosities of the samples were measured using an AR-G2 cone and plate rheometer at 25° C. with data reported at a shear rate of 1000/s. Data in FIG. 6 show that PVP K12, which has a lower average molecular weight relative to PVP K17, was a more effective viscosity-reducing excipient than PVP K17 at equivalent concentrations.

Example 7—mAb Stability in Formulations Comprising PVP K12

An experiment was performed to assess the effect of 2% PVP K12 on the stability of several mAbs. mAbs (including mAb5, an IgG2) were dialyzed against 15 mM sodium acetate pH 5.2.

Figure 7:
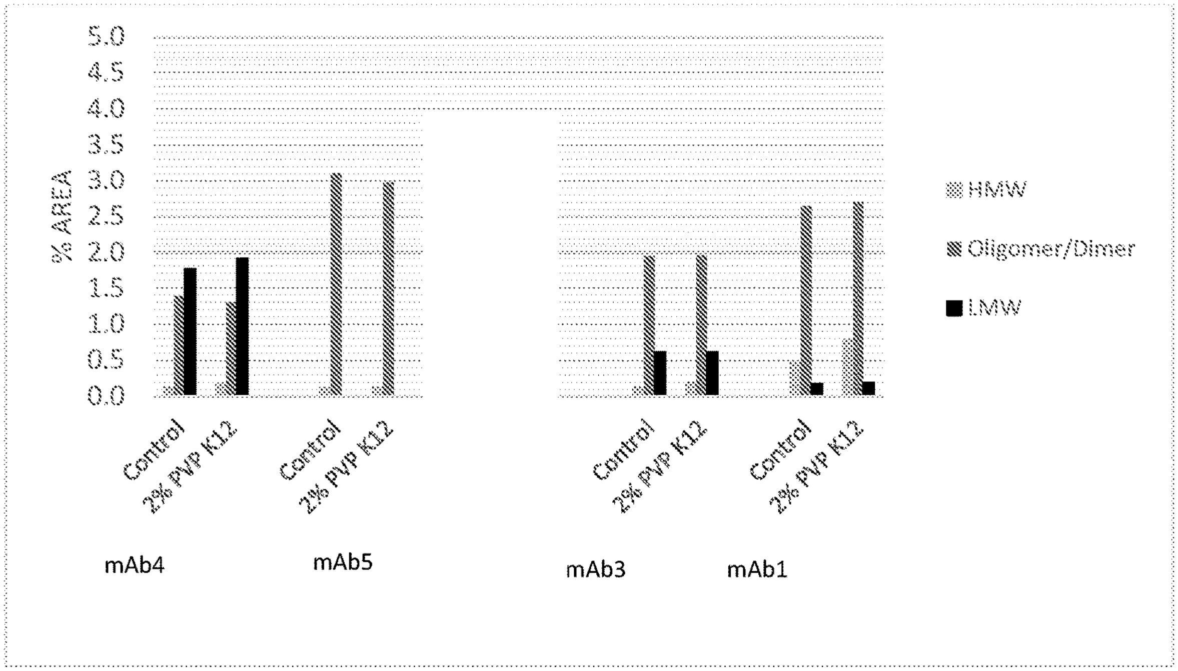
FIG. 7 shows a graph of the appearance of high molecular weight (HMW), low molecular weight (LMW) species and oligomers and dimers of high concentration of mAbs (mAbs 1, 3, 4, and 5) in the presence of PVP K12.

Following dialysis, PVP K12 was spiked in to a final concentration of 2%. mAb concentrations were adjusted to 100 mg/mL and samples were incubated at 40° C. for 2 weeks prior to analysis by size-exclusion high-performance liquid chromatography (SE-HPLC). FIG. 7 shows a graph of SE-HPLC area for several degradants for 2% PVP K12 mAb samples compared to controls spiked with water. These results indicate that 2% PVP K12 did not have a significant impact on mAb stability. This observation suggests that the viscosity-reducing effects can be applied without the induction of any significant increase in aggregation or clipping.

Definitions

"Viscosity" is a fluid's resistance to flow and can be measured in units of centipoise (cP) or milliPascal-second (mPa·s), where 1 cP=l mPa-s, at a given shear rate. Viscosity may be measured by using a viscometer, e.g., Brookfield Engineering Dial Reading Viscometer, model LVT (AMETEK Brookfield; Middleboro, MA), and AR-G2 cone and plate rheometer (TA Instruments; New Castle, DE). In some cases, viscosity is measured at 25 ° C. and reported at a shear rate of 1000/s. Viscosity may be measured using any other methods and in any other units known in the art (e.g. absolute, kinematic or dynamic viscosity), understanding that it is the percent reduction in viscosity afforded by use of the excipients described by the invention that is important. Regardless of the method used to determine viscosity, the percent reduction in viscosity in excipient formulations versus control formulations will remain approximately the same at a given shear rate.

An amount or concentration effective to reduce viscosity (a "viscosity-reducing amount") of an excipient means that the viscosity of the formulation in its final form for administration (if a solution, or if a powder, upon reconstitution with the intended amount of diluent) is at least 5% less than the viscosity of an appropriate control formulation, such as water, buffer, other known viscosity-reducing agents such as salt, etc. and those control formulations, for example, exemplified herein. Excipient-free control formulations might also be used even if they may not be implementable as a therapeutic formulation due to hypotonicity, for instance.

Similarly, a "reduced viscosity" formulation is a formulation that exhibits reduced viscosity compared to a control formulation.

A "pharmaceutical formulation" or a "pharmaceutical composition" is a sterile composition of a pharmaceutically active drug, such as a biologically active protein, that is suitable for parenteral administration (including but not limited to intravenous, intramuscular, subcutaneous, aerosolized, intrapulmonary, intranasal or intrathecal) to a patient in need thereof and includes only pharmaceutically acceptable excipients, diluents, and other additives deemed safe by the Federal Drug Administration or other national regulatory authorities. Pharmaceutical formulations include liquid, e.g. aqueous, solutions that may be directly administered, and lyophilized powders which may be reconstituted into solutions by adding a diluent before administration. Specifically excluded from the scope of the term "pharmaceutical formulation" are compositions for topical administration to patients, compositions for oral ingestion, and compositions for parenteral feeding.

"Shelf-life" means the storage period during which an active ingredient, such as a therapeutic protein, in a pharmaceutical formulation has minimal degradation (e.g., not more than about 5% to 10% degradation) when the pharmaceutical formulation is stored under specified storage conditions, for example, 2-8° C. Techniques for assessing degradation vary depending upon the identity of the protein in the pharmaceutical formulation. Exemplary techniques include size-exclusion chromatography (SEC)-HPLC to detect, e.g., aggregation, reverse phase (RP)-HPLC to detect, e.g. protein fragmentation, ion exchange-HPLC to detect, e.g., changes in the charge of the protein, mass spectrometry, fluorescence spectroscopy, circular dichroism (CD) spectroscopy, Fourier transform infrared spectroscopy (FT-IR), and Raman spectroscopy to detect protein conformational changes. All of these techniques can be used singly or in combination to assess the degradation of the protein in the pharmaceutical formulation and determine the shelf life of that formulation. Pharmaceutical formulations preferably exhibit not more than about 5 to 10% increases in degradation (e.g., fragmentation, aggregation or unfolding) over two years when stored at 2-8° C. "High molecular weight species" or "HMW species" means, in the context of a pharmaceutical formulation containing a therapeutic polypeptide, therapeutic proteins that are larger than the original therapeutic polypeptide, as determined by art-accepted assays. HMW species include oligomers of therapeutic polypeptides and aggregates of therapeutic polypeptides.

"Low molecular weight species" or "LMW species" means, in the context of a pharmaceutical formulation containing a therapeutic polypeptide, polypeptides that are smaller than the original therapeutic polypeptide, as determined by art-accepted assays. LMW species include fragments of the therapeutic polypeptide.

"Stable pharmaceutical formulation," "stable formulation" or "a pharmaceutical formulation is stable" refers to a pharmaceutical formulation that exhibit limited increased aggregation and/or reduced loss of biological activity of not more than 5% when stored at about −30° C. (or colder) to about 5° C. to about 40° C. for at least 1 month, or 2 months, or 3 months, or 6 months, or 1 year, or 2 years, or 5 years, or longer when compared to a control formulation sample. Formulation stability can be determined by a person of skill in the art using any number of standard assays, including size-exclusion HPLC (SEC-HPLC), cation-exchange HPLC (CEX-HPLC), Subvisible Particle Detection by Light Obscuration ("HIAC") and/or visual inspection. Typically, the warmer the storage temperature, the shorter the shelf life of the formulation.

Techniques for assessing degradation vary depending upon the identity of the protein in the pharmaceutical formulation. Exemplary techniques include size-exclusion chromatography (SEC)-HPLC to detect, e.g., aggregation, reverse phase (RP)-HPLC to detect, e.g. protein fragmentation, ion exchange-HPLC to detect, e.g., changes in the charge of the protein, mass spectrometry, fluorescence spectroscopy, circular dichroism (CD) spectroscopy, Fourier transform infrared spectroscopy (FT-IR), and Raman spectroscopy to detect protein conformational changes. All of these techniques can be used singly or in combination to assess the degradation of the protein in the pharmaceutical formulation and determine the shelf life of that formulation. Pharmaceutical formulations disclosed herein typically exhibit not more than about 2% to about 5% increases in degradation (e.g., fragmentation, aggregation or unfolding) over two years when stored at 2-8° C.

"Lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

"Diluent" refers to a substance that aids the formulation and/or administration of an active agent to and/or absorption by a patient and can be included in the disclosed compositions without causing a significant adverse effect on the patient. An example of a diluent is water, preferably sterile and purified.

"Arginine salt" means a salt of arginine. Examples include arginine monohydrochloride (Arg HCl), arginine acetate (Arg acetate) and arginine glutamate (Arg glutamate).

"N-acetyl arginine" (NAR) means the molecule of formula 1.

(1)

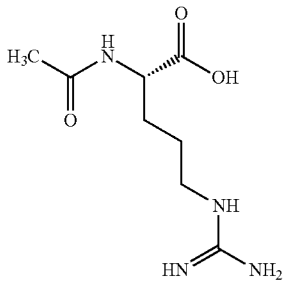

A "polypeptide," also known as a "protein," are used interchangeably. Exemplary polypeptides include antibodies, peptibodies, immunoglobulin-like proteins, non-antibody proteins and non-immunoglobulin-like proteins. Analogs of naturally occurring proteins are contemplated for inclusion in formulations of the present invention, including polypeptides with modified glycosylation, polypeptides without glycosylation (unglycosylated). "Protein analog" refers to an amino acid sequence that has insertions, deletions or substitutions relative to the parent sequence, while still substantially maintaining the biological activity of the parent sequence, as determined using biological assays known to one of skill in the art. Derivatives of naturally occurring or analog polypeptides which have been chemically modified, for example, to attach water soluble polymers (e.g., pegylated), radionuclides, or other diagnostic or targeting or therapeutic moieties.

A "therapeutic protein" is a protein (or "therapeutic polypeptide," the terms are used interchangeably) that has at least on therapeutic (beneficial) effect for a patient.

Therapeutic proteins include antibodies and related molecules. "Antibody" or "immunoglobulin" refers to a tetrameric glycoprotein that consists of two heavy chains and two light chains, each comprising a variable domain (V) and a constant domain (C). "Heavy chains" and "light chains" refer to substantially full-length canonical immunoglobulin light and heavy chains; the variable domains (VL and VC) of the heavy and light chains constitute the V region of the antibody and contributes to antigen binding and specificity. "Antibody" includes monoclonal antibodies, polyclonal antibodies, chimeric antibodies, human antibodies, and humanized antibodies. Light chains can be classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including IgG1, IgG2, IgG3, and IgG4. 1gM has subclasses including IgM1 and IgM2. IgA is similarly subdivided into subclasses including IgA1 and IgA2. Within full-length light and heavy chains, typically, the variable and constant regions are joined by a "J" region of about 12 or more amino acids, with the heavy chain also including a "D" region of about 10 more amino acids. The variable regions of each light/heavy chain pair typically form the antigen binding site. “Monoclonal antibody” refers to an antibody obtained from a population of substantially homogeneous antibodies, i.e., the individual antibodies comprising the population are identical except for possible naturally occurring mutations that may be present in minor amounts.

“Antibody variants” include antibody fragments and antibody-like proteins with changes to structure of canonical tetrameric antibodies. Typical antibody variants include V regions with a change to the constant regions, or, alternatively, adding V regions to constant regions, optionally in a non-canonical way. Examples include multi-specific antibodies (e.g., bispecific antibodies, trispecific antibodies), antibody fragments that can bind an antigen (e.g., Fab', F'(ab)2, Fv, single chain antibodies, diabodies), biparatopic and recombinant peptides comprising the forgoing as long as they exhibit the desired biological activity.

Multi-specific antibodies target more than one antigen or epitope. For example, a “bispecific,” “dual-specific”, or “bifunctional” antibody is a hybrid antibody that has two different antigen binding sites. Bispecific antibodies can be produced by a variety of methods including fusing hybridomas or linking Fab' fragments (Kostelny et al 1992, Songsivilai & Lachmann 1990, Wu & Demarest 2018). The two binding sites of a bispecific antibody each bind to a different epitope. Likewise, trispecific antibodies have three binding sites and bind three epitopes. Several methods of making trispecific antibodies are known and are being further developed (Wu & Demarest 2018, Wu et al 2018). DART (dual-affinity re-targeting molecules) are also examples of a multi-specific antibody.

BiTE® molecules: in some cases, a therapeutic protein is a bi-specific T-cell engager (BiTE) molecule. A BiTE molecule is a bispecific antibody construct or bispecific fusion protein comprising two antibody binding domains (or targeting regions) linked together. One arm of the molecule is engineered to bind with a protein found on the surface of cytotoxic T cells, and the other arm is designed to bind to a specific protein found primarily on tumor cell. When both targets are engaged, the BiTE molecule forms a bridge between the cytotoxic T cell and the tumor cell, which enables the T cell to recognize the tumor cell and fight it through an infusion of toxic molecules. The tumor-binding arm of the molecule can be altered to create different BiTE antibody constructs that target different types of cancer. The term “binding domain” in a BiTE molecule refers to a domain which (specifically) binds to/interacts with/recognizes a given target epitope or a given target site on the target molecules (antigens). The structure and function of the first binding domain (recognizing the tumor cell antigen), and preferably also the structure and/or function of the second binding domain (cytotoxic T cell antigen), is/are based on the structure and/or function of an antibody, e.g. of a full-length or whole immunoglobulin molecule. For example, the BiTE molecule comprises a first binding domain characterized by the presence of three light chain CDRs (i.e. CDR1, CDR2 and CDR3 of the VL region) and three heavy chain CDRs (i.e. CDR1, CDR2 and CDR3 of the VH region). The second binding domain preferably also comprises the minimum structural requirements of an antibody which allow for the target binding. More preferably, the second binding domain comprises at least three light chain CDRs (i.e. CDR1, CDR2 and CDR3 of the VL region) and/or three heavy chain CDRs (i.e. CDR1, CDR2 and CDR3 of the VH region). It is envisaged that the first and/or second binding domain is produced by or obtainable by phage-display or library screening methods rather than by grafting CDR sequences from a pre-existing (monoclonal) antibody into a scaffold. A binding domain may typically comprise an antibody light chain variable region (VL) and an antibody heavy chain variable region (VH); however, it does not have to comprise both. Fd fragments, for example, have two VH regions and often retain some antigen-binding function of the intact antigen-binding domain. Examples of (modified) antigen-binding antibody fragments include (1) a Fab fragment, a monovalent fragment having the VL, VH, CL and CH1 domains; (2) a F(ab')2 fragment, a bivalent fragment having two Fab fragments linked by a disulfide bridge at the hinge region; (3) an Fd fragment having the two VH and CH1 domains; (4) an Fv fragment having the VL and VH domains of a single arm of an antibody, (5) a dAb fragment (Ward et al 1989), which has a VH domain; (6) an isolated complementarity determining region (CDR), and (7) a single chain Fv (scFv), the latter being preferred (for example, derived from an scFV-library).

“Antibody fragments” include antigen-binding portions of the antibody including, for example, Fab, Fab', F(ab')2, Fv, domain antibody (dAb), complementarity determining region (CDR) fragments, CDR-grafted antibodies, single-chain antibodies (scFv), maxibodies (scFv-Fc), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), an antigen-binding-domain immunoglobulin fusion protein, single domain antibodies (including camelized antibody), a VHH containing antibody, or a variant or a derivative thereof, and polypeptides that contain at least a portion of an immunoglobulin that is sufficient to confer specific antigen binding to the polypeptide, such as one, two, three, four, five or six CDR sequences, as long as the antibody retains the desired binding activity.

REFERENCES

2014. Kollidon(R)—The Original. In BASF, ed. BASF: BASF

Ausubel F M. 1987. *Current protocols in molecular biology*. Brooklyn, N.Y. Media, Pa.: Greene Pub. Associates; J. Wiley, order fulfillment. 2 volumes (loose-leaf) pp.

Kamerzell T J, Esfandiary R, Joshi S B, Middaugh C R, Volkin D B. 2011. Protein-excipient interactions: mechanisms and biophysical characterization applied to protein formulation development. *Adv Drug Deliv Rev* 63: 1118-59

Kostelny S A, Cole M S, Tso J Y. 1992. Formation of a bispecific antibody by the use of leucine zippers. J Immunol 148: 1547-53

Powell M F, Nguyen T, Baloian L. 1998. Compendium of excipients for parenteral formulations. *PDA J Pharm Sci Technol* 52: 238-311

Sambrook J, Russell D W. 2001. *Molecular cloning: a laboratory manual*. Cold Spring Harbor, N.Y.: Cold Spring Harbor Laboratory Press.

Songsivilai S, Lachmann a 1990. Bispecific antibody: a tool for diagnosis and treatment of disease. *Clin Exp Immunol* 79: 315-21

Ward E S, Gussow D, Griffiths A D, Jones P T, Winter G. 1989. Binding activities of a repertoire of single immunoglobulin variable domains secreted from *Escherichia coli*. *Nature* 341: 544-6

Wu X, Demarest Si. 2018. Building blocks for bispecific and trispecific antibodies. *Methods*

Wu X, Yuan R, Bacica M, Demarest Si. 2018. Generation of orthogonal Fab-based trispecific antibody formats. *Protein Eng Des Sel* 31: 249-56

Unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See for example Ausubel et al (1987 et seq.) and Sambrook et al (2001) (Ausubel 1987, Sambrook & Russell 2001). Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

All patents and other publications identified are expressly incorporated herein by reference in their entirety for describing and disclosing, for example, the methodologies described in such publications that might be used in connection with the described.

The invention claimed is:

1. A method of reducing the viscosity of a pharmaceutical formulation comprising a therapeutic protein at a concentration, wherein said concentration is at least 70 mg/mL, the method comprising combining the therapeutic protein with a viscosity-reducing concentration of polyvinylpyrrolidone (PVP), thereby producing a reduced viscosity formulation that comprises the therapeutic protein at said concentration, wherein the PVP has an average molecular weight of 2,000 Da to 25,000 Da.

2. The method of claim 1, wherein the viscosity of the reduced viscosity formulation is less than or equal to 80 cP.

3. The method of claim 1, wherein the concentration of the therapeutic protein is 70 mg/mL to 300 mg/mL.

4. The method of claim 1, wherein the PVP is present in the reduced viscosity formulation at a concentration of 0.3% to 10%.

5. The method of claim 1, wherein the therapeutic protein is an antibody.

6. The method of claim 1, wherein the reduced viscosity formulation further comprises arginine.

7. The method of claim 1, wherein the concentration of the therapeutic protein is 140 mg/mL to 250 mg/mL.

8. The method of claim 1, wherein the PVP has a K value of 12-17.

9. The method of claim 6, wherein the arginine is N acetyl arginine.

10. The method of claim 6, wherein the arginine is Arg HCI and is present at about 67 mM, and wherein the PVP is present in the reduced viscosity formulation at about 1%.

11. The method of claim 1, wherein the viscosity of the pharmaceutical composition and the reduced viscosity formulation is a viscosity at 25° C. and at a shear rate of 1000/s.

12. The method of claim 4, wherein the therapeutic protein is an IgG2 monoclonal antibody, and said concentration is 70 mg/mL to 300 mg/mL.

13. A method of reducing the viscosity of a pharmaceutical formulation comprising a monoclonal antibody at a concentration, wherein said concentration is at least 70 mg/mL, the method comprising combining the monoclonal antibody with PVP, the PVP having a K value of 12-17, thereby producing a reduced viscosity formulation comprising the therapeutic protein at said concentration, wherein the viscosity of the reduced viscosity formulation is at least 10% lower than a control formulation lacking PVP.

14. The method of claim 13, wherein the concentration of the PVP in the reduced viscosity formulation is 0.3% to 10%.

15. The method of claim 1, wherein the reduced viscosity formulation has a viscosity that is at least 5% lower than a control formulation lacking PVP.

* * * * *